United States Patent [19]
Viertl

[11] Patent Number: 5,430,376
[45] Date of Patent: Jul. 4, 1995

[54] COMBINED THERMOELECTRIC AND EDDY-CURRENT METHOD AND APPARATUS FOR NONDESTRUCTIVE TESTING OF METALLIC OF SEMICONDUCTOR COATED OBJECTS

[75] Inventor: John R. M. Viertl, Niskayuna, N.Y.

[73] Assignee: General Electric Company, Schenectady, N.Y.

[21] Appl. No.: 73,468

[22] Filed: Jun. 9, 1993

[51] Int. Cl.⁶ .............................................. G01N 27/90
[52] U.S. Cl. ................................. 324/227; 324/226; 324/237; 324/238; 324/240; 324/242
[58] Field of Search ............... 324/227, 226, 451, 237, 324/238, 240, 242

[56] References Cited

U.S. PATENT DOCUMENTS

| | | |
|---|---|---|
| 2,972,882 | 2/1961 | Erwin . |
| 3,984,768 | 10/1976 | Staples . |
| 4,495,587 | 1/1985 | Plante et al. . |
| 4,542,345 | 9/1985 | Tomasulo . |
| 4,675,605 | 6/1987 | Watjen . |
| 4,706,020 | 11/1987 | Viertl et al. . |
| 4,739,261 | 4/1988 | Sugiyama et al. . |
| 4,763,274 | 8/1988 | Junker et al. . |
| 4,806,863 | 2/1989 | White . |
| 4,855,677 | 8/1989 | Clark, Jr. et al. . |
| 4,920,319 | 4/1990 | Viertl . |
| 4,965,519 | 10/1990 | Tornblom . |
| 4,989,154 | 1/1991 | Yamashita et al. . |
| 5,019,777 | 5/1991 | Gulliver et al. . |
| 5,021,738 | 6/1991 | Vernon et al. . |
| 5,028,100 | 7/1991 | Valleau et al. . |
| 5,030,911 | 7/1991 | Lam ............................ 324/242 |
| 5,055,784 | 10/1991 | Jaeger et al. . |
| 5,089,903 | 10/1991 | Otaka et al. . |

Primary Examiner—Kenneth A. Wieder
Assistant Examiner—Komrosh Cyrus Khosravi
Attorney, Agent, or Firm—Nixon & Vanderhye

[57] ABSTRACT

A microcomputer or PC based non-destructive coated-object testing system and method combines thermoelectrically measured surface coating thickness data with flaw/crack depth data determined from eddy current measurements of the surface of the object to locate and selectively identify faults or cracks which penetrate the surface coating. The microcomputer controls scanning of eddy-current and thermoelectric probes over the object surface and stores measured data along with surface coordinate information to provide a color-keyed graphics display of surface conditions for visual analysis.

8 Claims, 7 Drawing Sheets

COMBINED THERMOELECTRIC AND EDDY-CURRENT METHOD AND APPARATUS FOR NONDESTRUCTIVE TESTING OF METALLIC OF SEMICONDUCTOR COATED OBJECTS

FIELD OF THE INVENTION

This invention relates generally to a method and apparatus for detecting and characterizing surface coating flaws or cracks in various metallic and semi-conductive materials. In particular, the invention relates to a combined thermoelectric and eddy-current testing system for measuring coating thickness and determining the depth of detected cracks in the surface of a turbine bucket or any part with a metallic coating.

BACKGROUND OF THE INVENTION

In numerous applications, thin coatings of alloy materials are used on metal structures to protect them from the detrimental effects of high temperatures and/or corrosive environments. For example, in a gas turbine engine the turbine buckets (i.e., the turbine blades) and other components must be able to withstand exposure to extreme high temperature-high velocity corrosive gas streams. A protective coating on all components exposed to the gas stream is necessary to insure the longevity and satisfactory performance of the turbine. In many conventional turbines, the protective coating is developed from a class of alloys known as MCrAlY coatings, wherein M is selected from the group of metals consisting of cobalt, iron, nickel and mixtures thereof. Such coating compositions are well known in the art, as described, for example, in U.S. Pat. No. 4,419,416. Vacuum plasma sprayed coatings employing platinum-aluminum compositions (e.g., LDC-2E) are also known and used.

Some of the problems inherent in the manufacturing and refinishing of components having protective metal alloy coatings are discussed by the present inventor in U.S. Pat. No. 4,920,319. For example, in manufacturing new components having protective metallic or semiconductive material coatings and for deciding whether to rework such existing coatings when servicing used components, it is desirable to be able to determine both the thickness of the coating over the surface of the component and the presence of any cracks in the coating. Specifically, coatings on gas turbine buckets and other metal components are subject to thickness variations during manufacture and to the development of craze cracks during service which may penetrate into the bucket substrate material itself. It follows that in both the original manufacture and in refurbishing of turbine buckets, it is important to know the thickness of the bucket coating at all surface points as well as the location and depth of any existing coating cracks in order to determine whether the cracks penetrate the coating into the underlying bucket substrate material. Knowing such information, one can make informed decisions regarding the quality of the manufacturing process or the need for bucket repair. For example, if a crack penetrates the surface only to the extent of the coating thickness, the flaw can be remedied by a chemical stripping process that removes the coating and prepares the part for re-coating.

For obvious practical and economic reasons, it is most desirable to obtain such information using nondestructive testing methods. However, conventional nondestructive inspection methods are not capable of such comprehensive evaluations of coated components. For example, a fluorescent penetrant is used in one conventional method for nondestructive testing of such parts. However, using this method, parts with coating craze cracks typically show innumerable fluorescent crack indications rendering a comprehensive analysis impractical. Moreover, this conventional method is incapable of determining either crack depth or coating penetration.

Although eddy current testing is capable of relating crack depth information, when used as a stand-alone inspection tool and without the benefit of coating thickness information, it cannot determine whether or not a crack has penetrated the coating into the underlying substrate. Similarly, conventional thermoelectric testing methods provide only coating thickness information. As such, comprehensive information concerning characteristics of the coating and any cracks in it cannot be readily determined from a single methodology.

It is therefore an object of the invention to provide a computerized thermoelectric and eddy current combined test system for nondestructive testing of metallic or semiconductive material coated (or coated and diffused) components. It is a further object of the invention to provide a computerized system for the collection, analysis, evaluation and display of material surface coating thickness and surface flaw data for turbine or other machine components. It is also a further object of the invention to provide an improved eddy current probe design for use in such testing systems to obtain accurate eddy current measurements along a leading or trailing edge of a turbine bucket.

In accordance with a preferred exemplary embodiment of the present invention, a method and apparatus is provided for the acquisition and the correlation of eddy current test data with other forms of measured test data so that a more comprehensive analysis of the condition of a gas turbine bucket is possible. In particular, eddy current data obtained from a surface scan of a turbine bucket is combined and correlated with thermoelectric scan data of the same bucket surface. Surface scanning on separate occasions by eddy current and thermoelectric probes is computer controlled to obtain an exact correspondence between recorded data and the surface position of each probe during each scan. In addition to providing scan control and coordinate information for the probes, the testing system computer controls data collection, data storage (e.g., on a hard disk or an optical disk for archival purposes), data reduction, and production or display of data in various selectable forms such as charts, graphs, color-coded surface maps or printed hard copies.

DETAILED DESCRIPTION OF THE DRAWINGS

Figure 1:
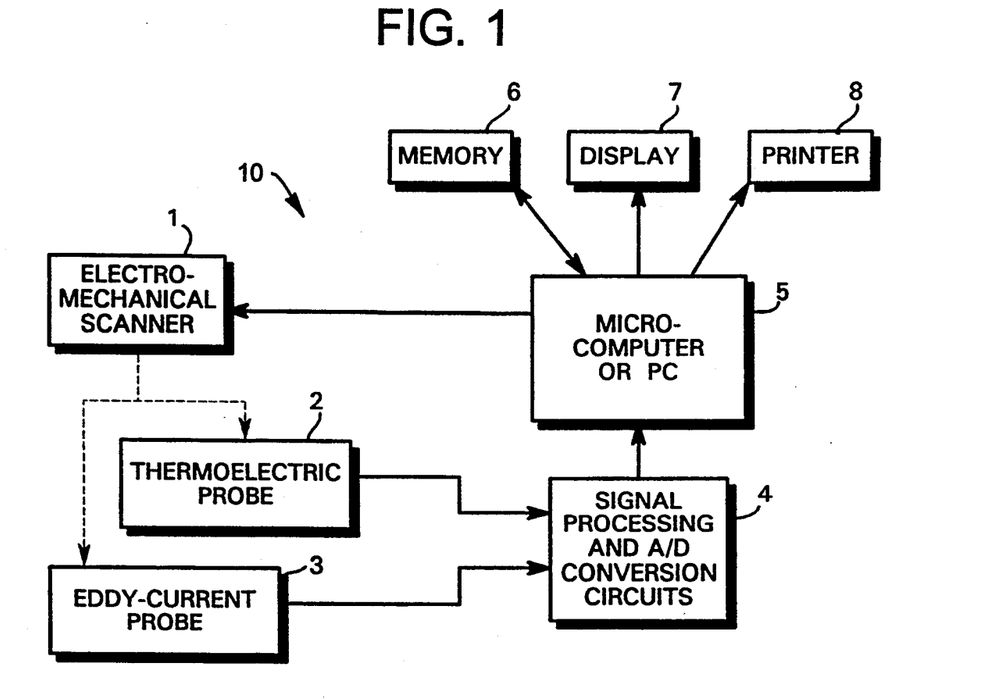
FIG. 1 is a block diagram illustrating a combined eddy-current and thermoelectric measurement system in accordance with a preferred exemplary embodiment of the present invention.

Referring to FIG. 1, a block diagram illustrates a combined eddy-current and thermoelectric test system 10 in accordance with a preferred exemplary embodiment of the present invention. The component scanning arrangement operates under control of a microcomputer or PC based controller 5. Electromechanical scanner 1 utilizes a conventional electromechanical actuator arm (see diagram in FIG. 5) to manipulate a test probe and the x, y and $\theta$ motions provided by the scan table (see FIG. 2, x scanner is #21, y scanner is #22, $\theta$ scanner is #23) for scanning the surface of a component part or piece of equipment.

Thermoelectric and eddy-current measurements are taken either simultaneously or sequentially. Preferably, the component under test is scanned twice with specific thermoelectric and eddy-current type test probes being interchanged between successive scans.

Signals from thermoelectric and eddy-current probes 2 and 3 are provided to conventional analog signal processing and A/D conversion circuits 4 that include, for example, an electrical impedance measuring circuit for the eddy-current probe, amplifier and noise filter circuits for the thermoelectric probe, and analog-to-digital conversion circuits (not shown) for providing digital data to microcomputer 5. Digitized raw thermoelectric and eddy-current data from each scan is stored (as acquired) in memory 6, then subsequently correlated and combined by microcomputer 5 for providing a graphical output for visual analysis via display 7 or graphics printer 8.

Since eddy-current signals frequently contain considerable noise from both the motion of the scanner and from various other internal and external electronic sources, some amount of additional signal processing is often needed to remove the effect of such noise sources. Consequently, signal processing to reduce noise and enhance the desired signals is also accomplished by microcomputer 5 using various digital signal processing techniques implemented in software. For example, data from a particular scan line or from several adjacent scan lines can be compared, averaged or digitally filtered to improve signal-to-noise ratio. Moreover, the raw eddy-current data (or for that matter thermoelectric data) correlated to surface location coordinate data may be separately and easily combined with other forms of component data to produce a more comprehensive analysis. Alternatively, in another contemplated embodiment, testing system 10 is operated in a "threshold" mode, wherein only the thermoelectric signal differences between the coating and the substrate (indicative of the coating thickness) are needed. These difference signals are compared by microcomputer 5 against a predetermined reference value or "tolerance level" corresponding to the substrate base or a minimum acceptable coating thickness. The results of the comparison is used to provide a GO/NO-GO type output display for that particular component.

In accordance with a preferred embodiment of the the present invention, microcomputer 5 of eddy-current and thermoelectric test system 10 may be a relatively inexpensive commercially available personal computer (PC) system provided with conventional computer aided graphics (CAD) graphics display software. Conventionally, eddy-current data was displayed in "strip-chart" fashion either on paper or electronically on a CRT display. However, as contemplated in the present embodiment, output data generated by microcomputer 5 is used in conjunction with CAD graphics software to produce either "unfolded" flat or 3-D perspective color-keyed views of component surface conditions. For this purpose, display device 7 may be any suitable medium or high resolution graphics monitor. As contemplated, memory resources 6 utilize conventional random access mass storage devices (e.g., hard disk, flash memories, etc.) and may include digital optical disk storage medium for archival purposes.

Figure 2:
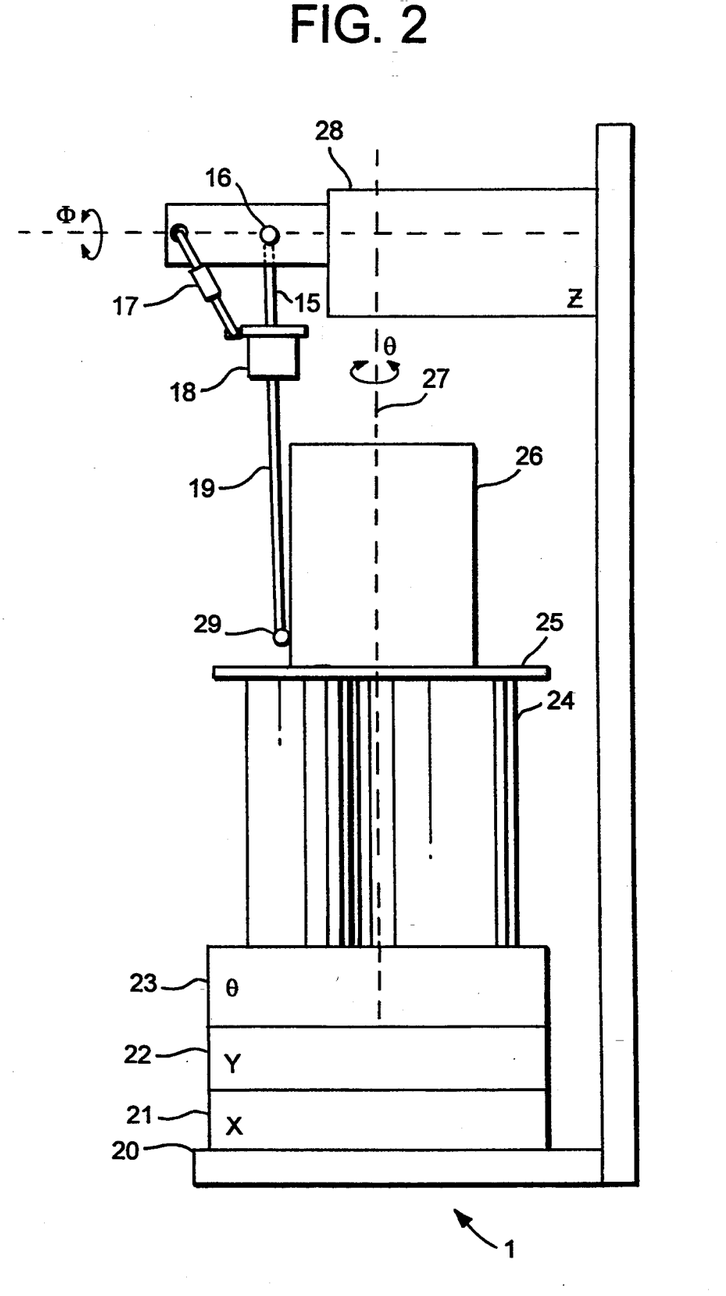
FIG. 2 is a diagrammatic illustration of the computer controlled mechanized scanning arrangement for use with both thermoelectric and eddy-current probes in accordance with the present invention.

FIG. 2 shows a diagrammatic illustration of an exemplary mechanized scanning arrangement for mechanical scanner 1 particularly adapted for scanning the surface of a turbine "bucket" (blade). Conventionally, a bucket consists of shank portion 24, tip portion 26 and platform portion 25. For the purposes of the present invention, the metallic coating on tip portion 26 is the feature of primary interest for testing. Accordingly, the bucket is preferably supported with its radial axis 27 oriented vertical (i.e., the bucket platform-to-tip direction) and is secured to scanner base table 20 by an appropriate means, as for example a dovetail clamp (not shown). A bucket support base table movement control mechanism (21, 22) produces X-axis and Y-axis translational motions of bucket 26 while probe support mechanism 28 provides the capability for Z-axis and rotational (i.e.,"Φ" direction) motions. Probe housing support arm 15 is rigidly attached at one end to probe housing 18 and is pivotally attached at 16 to support mechanism 28.

Probe housing 18 contains additional probe electronics such as an impedance reference coil for an eddy-current type probe or a rotational encoder for the preferred thermoelectric probe (discussed below). Housing 18 along with probe head 29 and probe arm 19 are removable to accommodate interchanging of thermoelectric type and eddy-current type probes. Probe actuator arm 17 is activated by microcomputer 5 and is spring loaded or appropriately biased so that a reasonably constant contact force is applied during scanning operations.

For eddy-current scan operations an additional movement control mechanism (23) included on support base 20 provides controlled rotation (i.e., "$\theta$" direction) about an axis which is parallel to the Z-axis or a vertical axis that includes the face of probe head 29. Also, during eddy-current scan operations there is a need to maintain a constant and precise clearance between the eddy-current probe head coil and the part/component surface being scanned. This clearance is relevant because it determines the amount of electromagnetic coupling between the probe coil and the surface material. Accordingly, the particular structure of the probe head used in obtaining eddy-current measurements is important as it affects this clearance and the resulting accuracy of the measurements. The composition of the eddy-current probe head is also important as it affects other considerations such as the desire to minimize probe head wear and reduce the amount of mechanical or vibrational noise induced into the system.

Figure 3A:
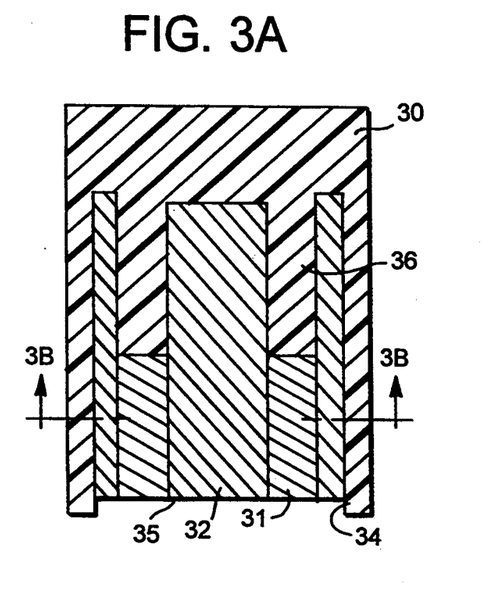
FIG. 3A is a cross-sectional side view of an exemplary eddy-current probe for scanning component surfaces.
Figure 3B:
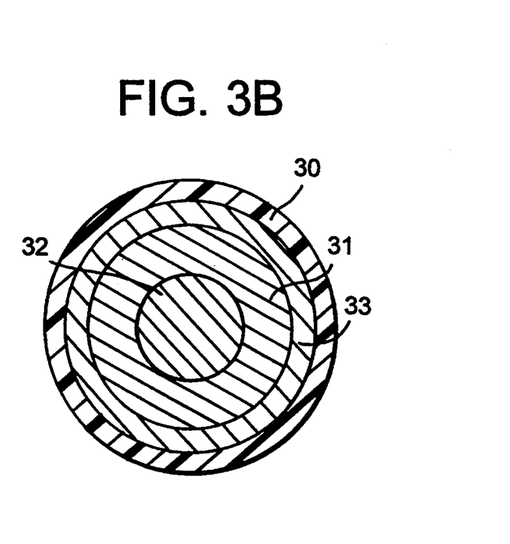
FIG. 3B is a cross-sectional bottom view of the eddy-current probe depicted in FIG. 3A.

Referring now to FIGS. 3A and 3B, a preferred exemplary embodiment of an eddy-current probe used for scanning flat-to-moderately curved surfaces (e.g., the airfoil surfaces of a turbine bucket tip) is shown. The probe transducer basically consists of a copper wire coil wound about a ferrite material core and surrounded by an outer ferrite material cylinder. Conventional ferrite materials such as ceramic manganese, zinc and iron compositions are used for the core and cylinder. This arrangement results in a circular magnetic flux-gap which provides omni-directional sensitivity and allows scanning in any direction. Although various types of eddy-current transducers can be used (e.g., multiple concentric or adjacent coil transducers), an "absolute eddy-current" transducer type probe is preferred because craze cracks are typically extremely close together. In addition, the preferred eddy-current probe transducer is one having a coil diameter that is approximately twice the expected nominal coating thickness of the part tested. This diameter is preferential because it enhances the crack sizing capability of the test and provides a response that is proportional only to crack depth, as explained in further detail below with respect to FIG. 6A.

FIG. 3A depicts a cross-sectional side view of the probe illustrating the internal construction. Probe body 30 is preferably composed a suitable polymer compound having low friction and self-lubricating properties (e.g., Delrin TM ). A self-lubricating polymer is used since, during scanning operations, the probe face is in constant contact with the scanned surface. Friction due to the constant rubbing causes the probe to wear rapidly and can cause vibrations which generate noise signals. The use of a probe body constructed of self-lubricating polymers significantly reduces vibrations and extends the useful life of the probe. Coil wire 31 is wound around lower half of ferrite material inner core 32 and is flush with probe face surface 35 (i.e., the probe face that is adjacent to the surface of the object under test). The coil is electrically connected to external sensing electronics via an integrally molded wire conductor pair (not shown) extending out through upper portion of probe body 30. Ferrite cylinder 33 surrounds coil wire 31 and is separated from inner core 32 by probe body portion 36. A portion of probe body 30 protrudes slightly beyond bottom probe face surface 35 to form an annular ridge or lip 34. The annular ridge may be rounded or flat (as depicted in FIG. 3A) and serves to provide a predetermined constant clearance or "lift-off" between coil 31 and a surface being scanned. It is important to maintain the distance between the transducer face and the scanned surface constant since the eddy-current transducer response is directly related to this distance and, therefore, fluctuations or variations in this distance can result in lost or inaccurate measurements. FIG. 3B shows a cross-sectional view of the probe taken through coil wire 31.

Figure 4:
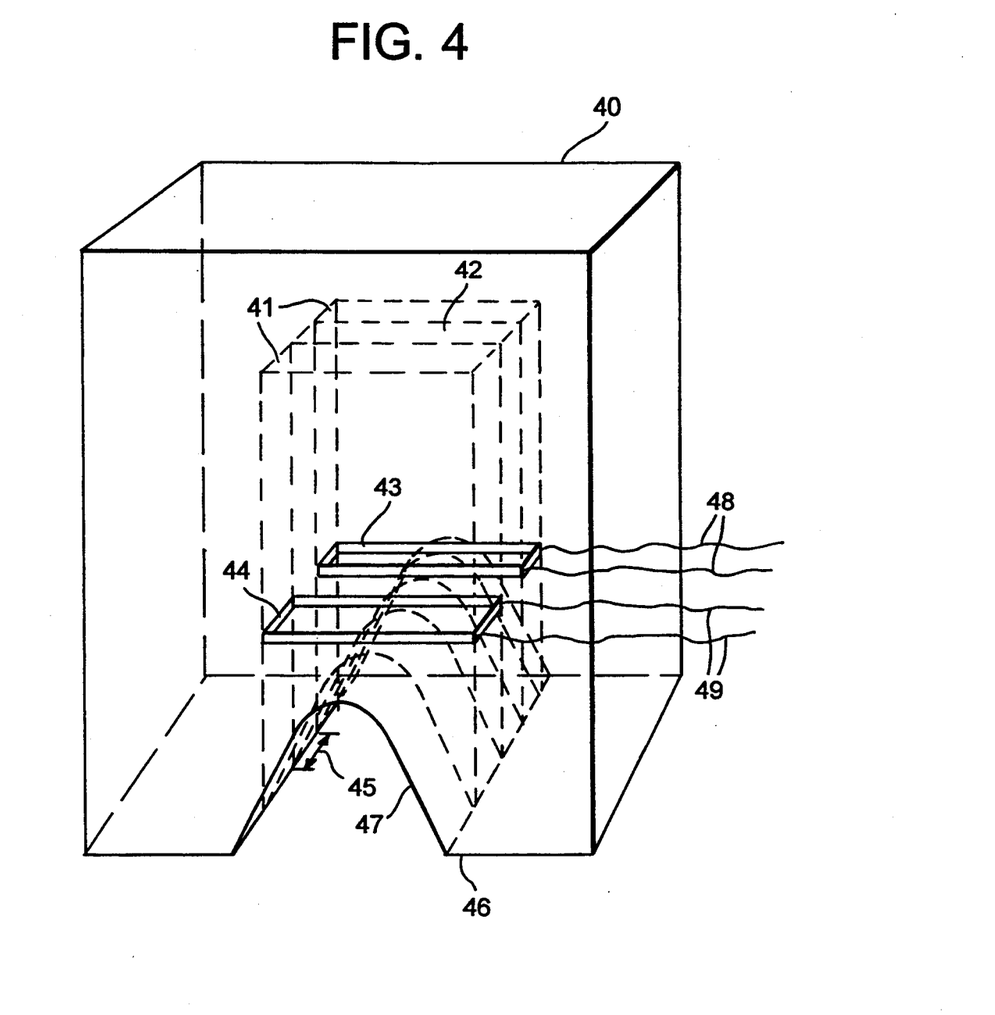
FIG. 4 is a transparent perspective view illustrating the construction of a preferred embodiment of an eddy-current "bucket edge" linear-gap probe for obtaining eddy-current measurements along turbine bucket leading and trailing edge surfaces.

FIG. 4 depicts a transparent perspective view illustrating the internal structure of an exemplary "bucket-edge" eddy-current linear-gap probe designed specifically for obtaining eddy-current measurements along the leading and trailing edges of a turbine bucket surface. For this purpose, the preferred eddy-current probe basically consists of a pair of rectangular ferrite cores 41 separated by a thin layer of magnetically inert material 42 such as plastic or an appropriate glue. Each ferrite core is surrounded by separate wire coils 43 and 44. This arrangement results in a linear magnetic flux-gap 45 (somewhat similar to conventional magnetic recording heads) which provides enhanced detection of craze cracks that wrap around the bucket edge.

Probe body 40 is composed of Delrin TM or similar material as discussed above. Probe face 46 has a concave contoured region, 47, to specifically match the surface curvature of particular turbine bucket edges. Ferrite cores 41 extend from slightly below the top portion of probe body 40, throughout contoured region 47, to probe bottom face 46. Coils 43 and 44 are positioned along the lower portions of ferrite cores 41, as close as possible to contoured region 47 to enhance probe sensitivity. This combination of a contoured face and the linear magnetic-gap configuration results in better electromagnetic coupling of the probe to bucket edge surfaces and provides improved resolution of surface cracks (which usually tend to be oriented perpendicular to the edge of the bucket airfoil surface and separated by only a few thousandths of an inch). Coils 43 and 44 each have a separate pair of wire conductor leads, 48 and 49, extending through probe body 40. This allows any electrical "unbalance" or parametric differences between the two coils to be easily checked and compensated before the probe is put to use. (Conventionally, one lead from each coil is common or electrically connected together).

For scanning operations conducted during the thermoelectric current measuring operations in accordance with the present invention, a thermoelectric probe of the "rolling ball" type, as described in U.S. Pat. No. 4,920,319, is preferred. The method and apparatus disclosed in the '319 patent for determining the thickness of a coating on a metal substrate is incorporated herein by reference.

Figure 5A:
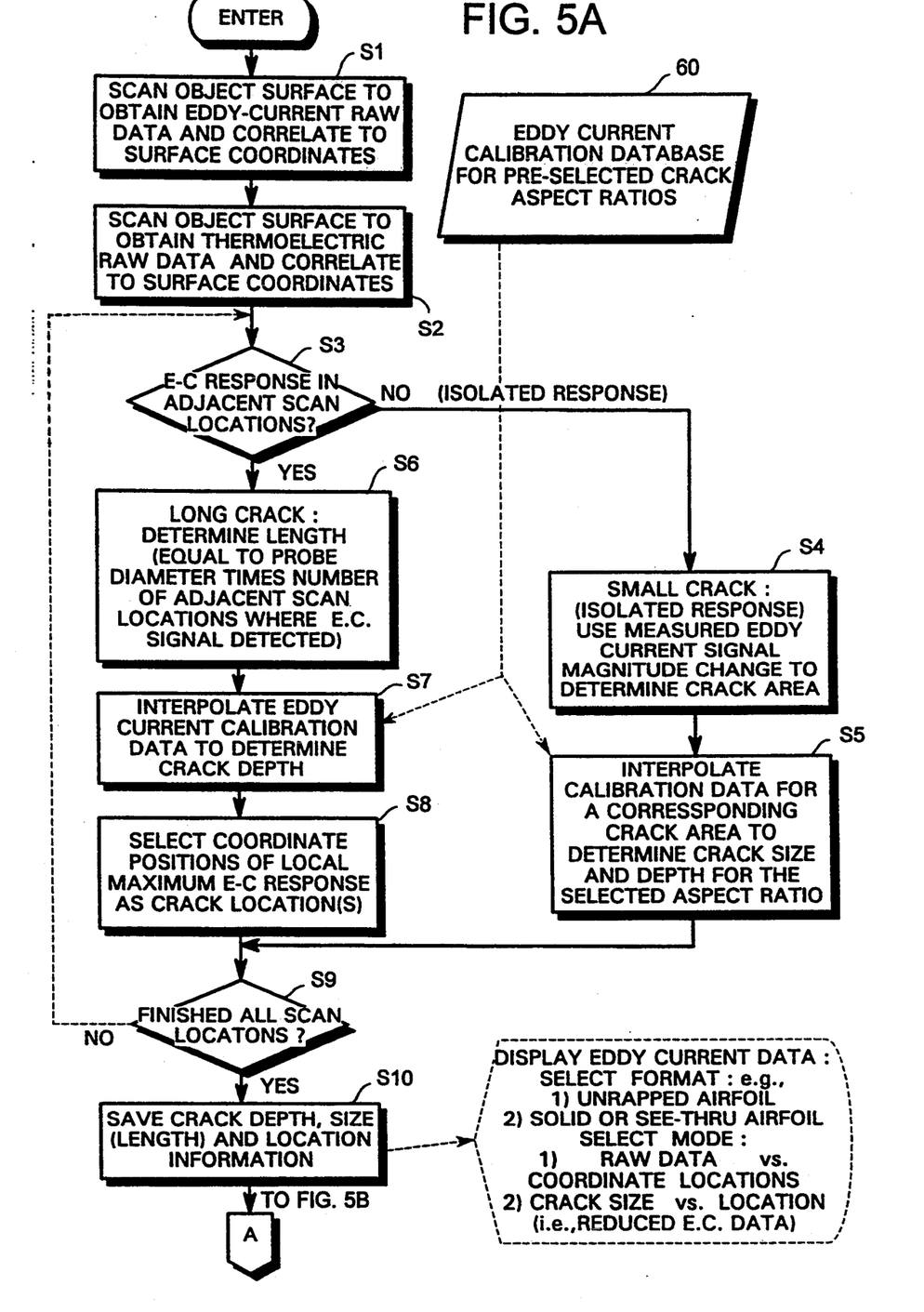
FIGS. 5A and 5B depict flowcharts showing exemplary steps for correlating, combining and displaying eddy-current and thermoelectric measurement data for surface coating evaluations in accordance with a preferred exemplary embodiment of the present invention.
Figure 5B:
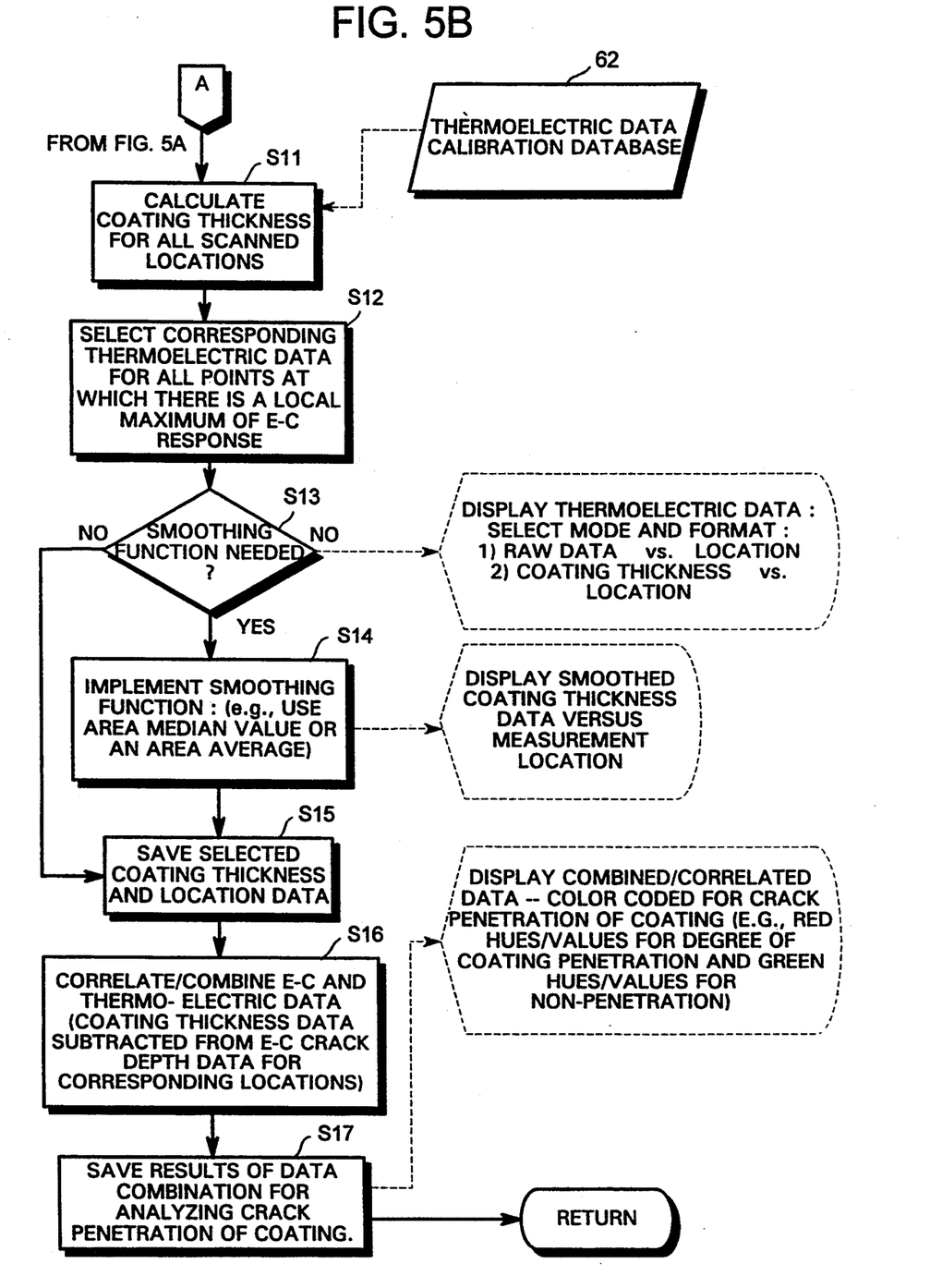

Referring now to FIGS. 5A and 5B, a schematic flowchart is shown that illustrates control steps in an exemplary program operable on microcomputer 5 for obtaining, correlating and combining both eddy-current and thermoelectric data for surface coating evaluations of an object. Step S1 of the flowchart calls for the surface of the object (e.g., a turbine bucket) to be scanned to obtain eddy-current raw data and to correlate to surface coordinates. Step S2 of the flowchart calls for the surface of the object to be scanned to obtain thermoelectric raw data and to correlate it to surface coordinates. Either step S1 or S2 may be performed first. However, antecedent to these steps (not shown) or at least inherent to the first step is the generation and utilization of a suitable coordinate system surface representation (e.g., Cartesian or other) of the particular object or part. Although a conventional coordinate measuring machine could be used for coordinate determination, it is typically too slow for scanning parts. Moreover, the surface scan speed of such a machine would also have to be carefully controlled or accurately measured.

Accordingly, the surface representation or "scan plan" needed for scanning a particular part under control of microcomputer 5 is preferably generated by using engineering drawing coordinate data created from a suitable CAD program or a computerized drafting system representation of the part. The scan plan can also be generated in the present system through a heuristic type learning process (e.g., "teaching" the system by manually moving actuator arm and probe assembly over the surface of the part while microcomputer 5 monitors and records the coordinates of the probe position via feedback from mechanical actuators/servos). This coordinate information can subsequently be used by microcomputer 5 to control movement of the probe during each scanning process. Alternatively, the scan plan could be generated by using a "contact detecting" probe and a scale-model drawing for the part. This type of probe employs an electrical sensing means to detect probe contact and probe tip movements. The scale drawing and the part are traced using the probe and the information thus obtained can then be used to determine differences between the part as designed and the actual or true part surface. This approach has the advantage of providing surface coordinates that can be easily corrected for any variations between the actual part and the part specifications or drawing.

With respect to FIG. 5A, scanning to acquire raw data in steps S1 and S2 of the flowchart is accomplished electromechanically under microcomputer control. As a part of these scanning steps, microcomputer 5 is also programmed to halt automated scanning at certain points to allow a manual changing of the particular probe head type being used (for example, to accommodate scanning the bucket edge surfaces or to switch from eddy-current to thermoelectric type probes).

During the eddy-current scan operations, an eddy-current probe response (i.e., a measured impedance change) is usually indicative of the presence of a crack at a particular location. For rapid isolated responses, the crack size is relatively small and is likely to be shorter in length than the diameter of the probe head. Conversely, responses measured at adjacent locations are usually indicative of a crack length greater than or equal to the diameter of the probe head. Accordingly, in step S3 of the flowchart, the coordinate correlated raw data acquired during the eddy-current scan is checked to determine whether any probe responses were detected at adjacent scan coordinate locations.

In accordance with the preferred method for determining coating penetration of the present invention, eddy-current data is analyzed differently according to the relative size of a detected crack. More specifically, when the size of a crack is such that the crack length is greater than or equal to the diameter of the eddy-current probe head (i.e., a "long" crack), the eddy-current data is analyzed by assuming that the eddy-current response due to this crack is at the maximum (because the crack is longer than the diameter of the eddy-current probe) and that the remaining eddy-current response is proportional only to crack depth. Conversely, if a surface coating crack is less than the diameter of the probe head, it is convenient to model the crack as having a classical "half-penny" shape; i.e., it can be interpreted as a crack having a length equal to twice the crack depth. This model, of course, assumes a crack length-to-depth aspect ratio of 2 to 1. Other aspect ratios could also be used in modeling the crack (e.g., depending on the result of metallographical investigations to determine the most probable aspect ratio to expect for a given material exposed to a given set of operational and environmental conditions). Considering the "half-penny" crack model and using an eddy-current probe diameter that is twice the expected nominal coating thickness, a crack having a surface length equal to the probe diameter would also necessarily have a depth that is equal to the coating thickness (i.e., just reaches to the nominal coating depth). Assuming good eddy-current coupling between the probe and the part surface, this implies that the responses to cracks which penetrate the coating would be at or close to the response expected for a "long" crack. Thus, as mentioned above, a judicious selection of the proper eddy-current probe diameter can result in an eddy-current probe response that is desirably proportional to crack depth only.

Referring again to FIG. 5A, for isolated eddy-current scan responses detected at step S3, the change in measured eddy-current signal magnitude (being proportional to the crack area) is used to determine the crack area at step S4. Next, in step S5, that value is used to access a data base of eddy-current crack responses, 60, to determine the size and depth of the measured crack. Data base 60 is preferably compiled from the results of previous eddy-current measurements of test samples of various materials which are recorded and calibrated against actual visual microscopic measurements. This data base is stored locally in memory 6 of microcomputer controller 5 (FIG. 1). Data base 60 contains a wide range of "calibrated" crack area values (corresponding to eddy-current responses), including values assuming a variety of different crack aspect ratios and for various types of coating materials. Moreover, to improve accuracy, crack size and depth values are obtained in step S5 by interpolating between values corresponding to the closest crack area values stored in data base 60.

If in step S3 eddy-current responses were found in adjacent locations, then it is assumed that the crack is a "long" crack and, in step S6, the length of the crack is determined (e.g., by multiplying the known diameter of the probe by the number of adjacent scan locations where an eddy-current response was detected). Next, in step S7, the calibrated eddy-current response information in data base 60 is accessed and interpolated to determine the "long" crack depth. Among a large group of neighboring coordinate responses, a set of coordinate positions of local maximum of eddy-current response is selected as the crack (center) location in step S8.

As indicated by step S9, the above processes are reiterated until all locations of the scanned object have been included. Next, in step S10, the depth, size (or length) and corresponding location coordinate information for all cracks detected is saved for other uses in later calculations (discussed below). Correlated information from the eddy-current scan operations may also be displayed at this time in either statistical or graphical form using a variety of display formats and display modes (e.g., "unwrapped airfoil", solid and see-thru airfoil formats; or raw data vs. coordinate location and crack size vs. coordinate location statistical graph modes).

Referring now to FIG. 5B, the calculation of coating thickness from thermoelectric scan raw data and the combination of coating thickness data with eddy-current crack data is discussed. (One knowledgeable in the art can appreciate that the steps for calculating coating thickness and the corresponding correlation of that data to surface coordinate locations may precede the processing of eddy-current data discussed above, if so desired.) As indicated in step S11, the coating thickness for all scanned locations is next calculated using "calibration" data from data base 62. Accordingly, thermoelectric raw data acquired during the thermoelectric scanning operations of step S2 is used to access calibration data stored in data base 62 for the particular metal coating-metal substrate combination being tested.

Preferably, the information in data base 62 is compiled from the results of previous thermoelectric measurements of certain "calibration specimens" (i.e., specimens of various metal coating-metal substrate combinations and of different coating thicknesses for the same coating/substrate combinations are measured both thermoelectrically and optically (e.g., via metallographical microscopy) to build a data base of calibrated thermoelectrical responses for a wide variety of coating/substrate combinations). The thermoelectric calibration data base (62) is preferably stored locally along with eddy-current calibration data base 60 in memory 6 of microcomputer controller 5 (FIG. 1). Using this information (as one might use a calibration curve), the coating thickness for various predetermined metal or semiconductor coated objects can then be calculated by an interpolation of thickness values for the closest corresponding thermoelectric responses. The resulting thickness values obtained will be accurate as long as the calibration data was made under the same scan conditions as the object under test.

Since the eddy-current data does not have as fine a spatial resolution as the thermoelectric data, the eddy-current responses from a neighborhood of measurements on a given crack are searched for the local maximum response, which is also used in determining the crack size (in steps S7 and S8). At step S12, since both thermoelectric and eddy-current data are known for a grid of measured positions on the part by direct measurement, the point or set of common points corresponding to a local maximum in eddy-current response is selected to obtain corresponding points in the thermoelectric data to use for evaluating whether or not complete coating penetration by a crack has occurred. Next, in step S13, if the corresponding thermoelectric data in the neighborhood of this point or set of points is found to be noisy, a local average or local median calculation is performed in step S14 to "smooth" or improve the thermoelectric data. (This type of smoothing function could be applied either to the raw data or to the coating thickness values.) Next, in step S15, coating thickness data for the selected locations is saved for future calculations and display (discussed below).

The next step, S16, calls for calculation of the difference between coating thickness values and crack depth values for the aligned (correlated) points in the two data sets. If the crack depth is greater than the coating thickness, then complete coating penetration is implied. If the crack depth is less than the coating thickness, then complete coating penetration is not implied. If the crack depth is equal to the coating thickness, then either one of the above implications can be assumed.

Figure 6:
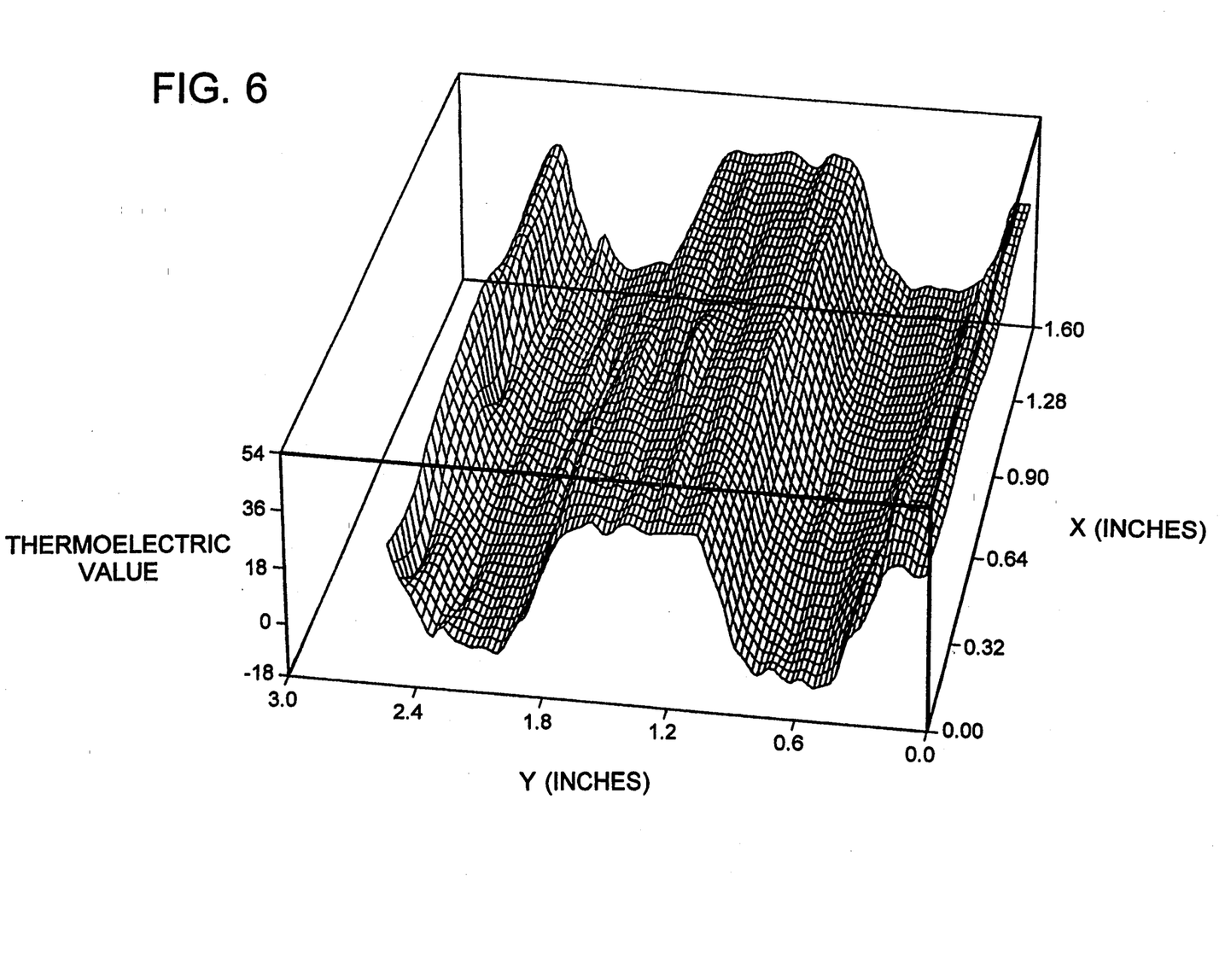
FIG. 6 is an illustration of an exemplary computer generated 3-D graphical plot of thermoelectric data values versus surface area obtained from scanning a platinum aluminide coated plate.
Figure 7A:
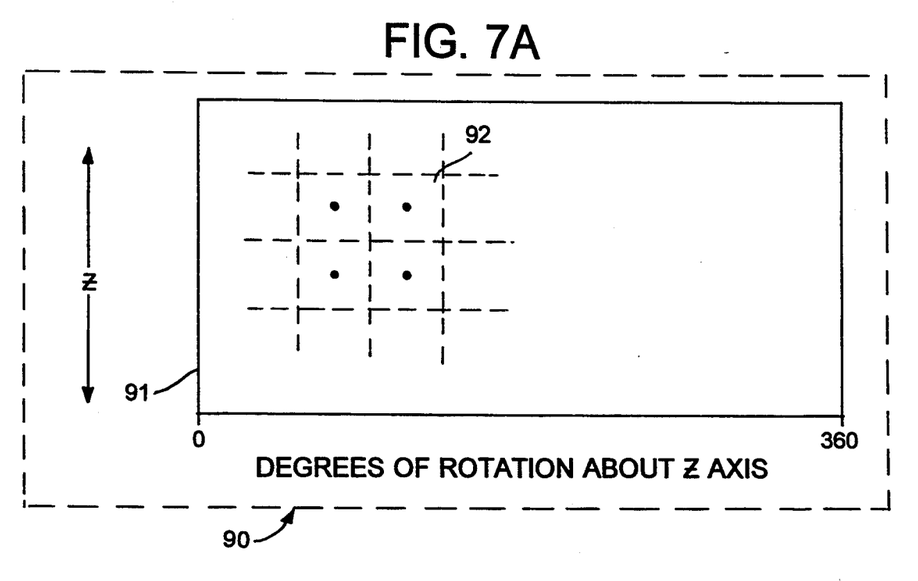
FIG. 7A is an illustration of an exemplary computer generated output display format using an unwrapped airfoil for depicting turbine bucket coating measurements.
Figure 7B:
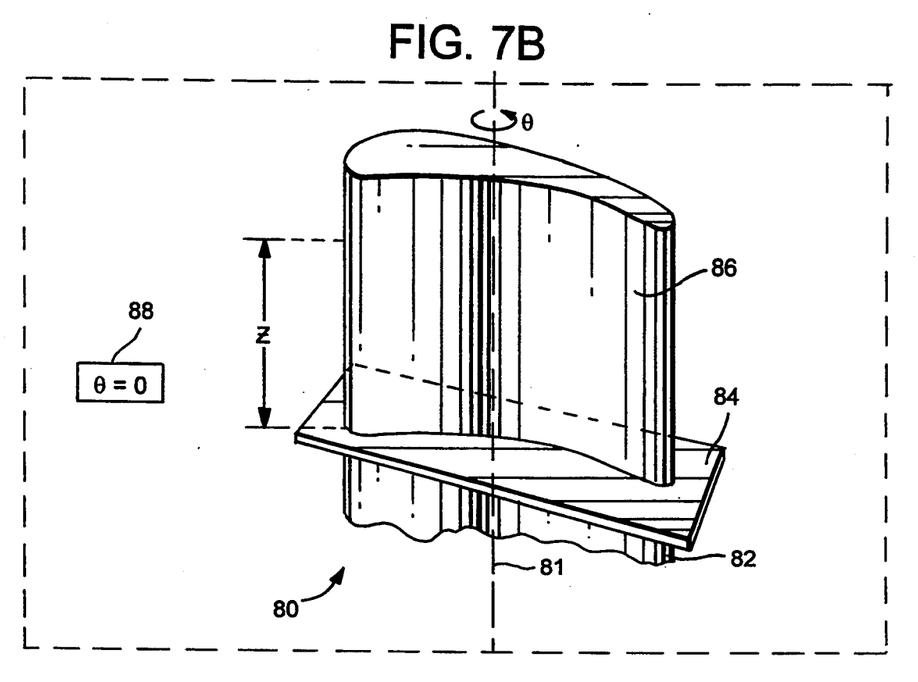
FIG. 7B is a illustration of an alternative computer generated display format using a solid model airfoil for depicting turbine bucket coating measurements.

In accordance with the present invention, the correlated and combined surface data may be selectively displayed in a variety of ways, either as raw statistics or as graphical displays utilizing those statistics, such as illustrated by FIGS. 6 thru 7B. For example, FIG. 6 illustrates an exemplary computer generated 3-D graphical display of thermoelectric data values, obtained from scanning the surface of a platinum-aluminide coated test plate, plotted vertically versus X-Y surface area coordinates. Alternatively, an "unwrapped" surface area map of the component showing the computed coating thickness and crack depth values color-coded according to different conditions can be displayed (e.g., coating penetration regions shown in red with the intensity of the red indicating the degree of penetration; similarly, another color, such as green, used to highlight those regions where a crack does not penetrate the coating). For example, FIG. 7A illustrates an exemplary computer generated output display format (90) showing an "unwrapped" turbine bucket airfoil. The Z axis (91) represents the bucket radial axis with surface characteristics displayed according to height above the bucket platform base. A set of color-coded zones 92 is used for depicting surface coating thickness and crack measurements.

FIG. 7B illustrates another preferred alternative exemplary computer generated output format in which a turbine bucket (80) under test is shown in a solid surface model representation. The bucket is displayed with its radial axis 81 in a vertical orientation and with shank portion 82 and platform portion 84 positioned at the the bottom. In this output format, bucket surface 86 is preferably displayed as color-coded according to the particular coating characteristic values measured or calculated at the corresponding locations on the surface. The displayed viewing angle, $\theta$, about the Z axis is adjustable (e.g., via conventional keyboard or other command input device at the microcomputer controller). A perspective meter 88 is also displayed to provide an indication of relative degrees of rotation of the viewing angle about the Z axis.

The presently-described flowcharts, FIGS. 5A and 5B for the measurement system, display various outputs which require operator interpretation. These results can be classified also either as acceptable or not based upon selected accept or reject threshold and limit criteria for the part. This calculation can be performed automatically and the results displayed to an operator.

Another form of presentation can be presented in the form of a table, listing the extent and location of the rejection regions. The entire evaluation process could be automated for accept/reject of the part being tested.

The invention has been described in connection with what is presently considered to be the most practical and preferred embodiment. The invention is not to be limited to the disclosed embodiment, but covers various modifications and equivalent arrangements included within the spirit and scope of the appended claims.

What is claimed is:

1. A system for combined thermoelectric and eddy-current nondestructive testing of metallic coating on a surface of an object, comprising:
 a first scanning probe for measuring surface thermoelectric conductivity characteristics indicative of the thickness of said coating;
 a second scanning probe for measuring surface eddy-current electromagnetic characteristics indicative of the presence and depth of a crack or flaw in said surface; and
 a microcomputer for correlating and combining thermoelectric and electromagnetic surface characteristic data acquired from said first and second probes to determine whether said crack or flaw has penetrated said coating.

2. The testing system of claim 1, further comprising:
an electromechanical scanning means for moving said first and said second probes in predetermined spatial scanning patterns over said coating, said electromechanical scanning means controlled by said microcomputer.

3. The testing system of claim 1, further comprising:
an output device connected to said microcomputer for providing a visual display of said characteristic data.

4. A system for combined thermoelectric and eddy-current nondestructive testing of semiconductor coating on an object surface, comprising:
thermoelectric probe means for measuring surface conductivity characteristics indicative of the thickness of said coating;
eddy-current probe means for measuring surface electromagnetic characteristics indicative of the presence and depth of a crack or flaw in said object surface;
electromechanical scanning means for moving said thermoelectric probe and said eddy-current probe over said coating; and
a digital processor means for controlling said electromechanical scanning means and for correlating and combining thermoelectric and electromagnetic surface characteristic data acquired from said eddy-current and thermoelectric probes to determine whether a crack or flaw has penetrated said coating.

5. A system as in claim 4, wherein said digital processor further comprises a means for generating surface model and graphical representations of said combined thermoelectric and electromagnetic surface characteristic data for visual display.

6. Method for combined thermoelectric and eddy-current nondestructive testing of a metallic coated object, said method comprising the following steps:
(a) scanning the outer surface of said object using an eddy-current transducer type probe to obtain electromagnetic data indicative of the presence and depth of a crack or flaw;
(b) scanning the outer surface of said object using a thermoelectric type probe to obtain conductivity data indicative of the thickness of a metallic or semiconductor coating on said object;
(c) correlating said electromagnetic data and said conductivity data to corresponding surface coordinates on said object;
(d) calculating the difference between selected corresponding values of said conductivity data and said electromagnetic data, said values selected according to coordinate locations of eddy-current data indicative of the presence of a crack or flaw.

7. The method of claim 6, further including the step of:
displaying said conductivity data and said electromagnetic data in a statistical or graphical manner correlated to surface location coordinates of said object.

8. The method of claim 6, further including the step of:
displaying said calculated difference values of conductivity and electromagnetic data, corresponding to surface locations where the depth of a crack is greater than or equal to the thickness of the coating, in a statistical or graphical manner correlated to surface location coordinates of said object.

* * * * *